United States Patent
Sim

(10) Patent No.: US 11,814,342 B2
(45) Date of Patent: Nov. 14, 2023

(54) METHANE TO METHANOL CONVERSION

(71) Applicant: Sediment Research & Minerals Ltd., Winnipeg (CA)

(72) Inventor: W. J. Frank Sim, Winnipeg (CA)

(73) Assignee: Sediment Research & Minerals Ltd., Winnipeg (CA)

( * ) Notice: Subject to any disclaimer, the term of this patent is extended or adjusted under 35 U.S.C. 154(b) by 0 days.

(21) Appl. No.: 17/702,077

(22) Filed: Mar. 23, 2022

(65) Prior Publication Data

US 2022/0306560 A1 Sep. 29, 2022

Related U.S. Application Data

(60) Provisional application No. 63/167,168, filed on Mar. 29, 2021.

(51) Int. Cl.
| | |
|---|---|
| *C07C 29/50* | (2006.01) |
| *B01J 27/24* | (2006.01) |
| *B01J 37/00* | (2006.01) |
| *B01J 29/06* | (2006.01) |
| *B01J 21/18* | (2006.01) |

(52) U.S. Cl.
CPC ............... *C07C 29/50* (2013.01); *B01J 21/18* (2013.01); *B01J 27/24* (2013.01); *B01J 29/06* (2013.01); *B01J 37/0036* (2013.01)

(58) Field of Classification Search
CPC .......... C07C 29/50; C07C 31/04; B01J 21/18; B01J 27/24; B01J 27/745
See application file for complete search history.

(56) References Cited

PUBLICATIONS

Cui, X. et al. "Room-Temperature Methane Conversion by Graphene-Confined Single Iron Atoms" CHEM, 2018, 4, 1902-1910; Jun. 14, 2018 (Jun. 14, 2018).
Li, Z. et al. "the Marriage of the FeN4 Moiety and MXene Boasts Oxygen Reduction Catalysis; Fe 3d Electron Delocalization Matters" Advanced Materials, 2018, 30(43), 1803220 Sep. 10, 2018 (Sep. 10, 2018).

*Primary Examiner* — Jafar F Parsa
(74) *Attorney, Agent, or Firm* — Adrian D. Battison; Ade & Company Inc.; Ryan W. Dupuis

(57) ABSTRACT

Single iron atoms embedded in graphene can catalyse the conversion of methane into methanol at room temperature. Dependent upon the flow of gas from the well, a reactor vessel will be built and housed in a building heated by the raw gas to a temperature of seventy degrees Fahrenheit. This catalyst is carried on a bed of zeolite which will remove nitrogen and nitrogen compounds in adsorption process, as well as some sulphur and a good percentage of carbon dioxide. Iron— nitrogen—carbon (Fe—N—C) acts as the most satisfactory alternatives to platinum for the oxygen reduction reaction (ORR).

20 Claims, 1 Drawing Sheet

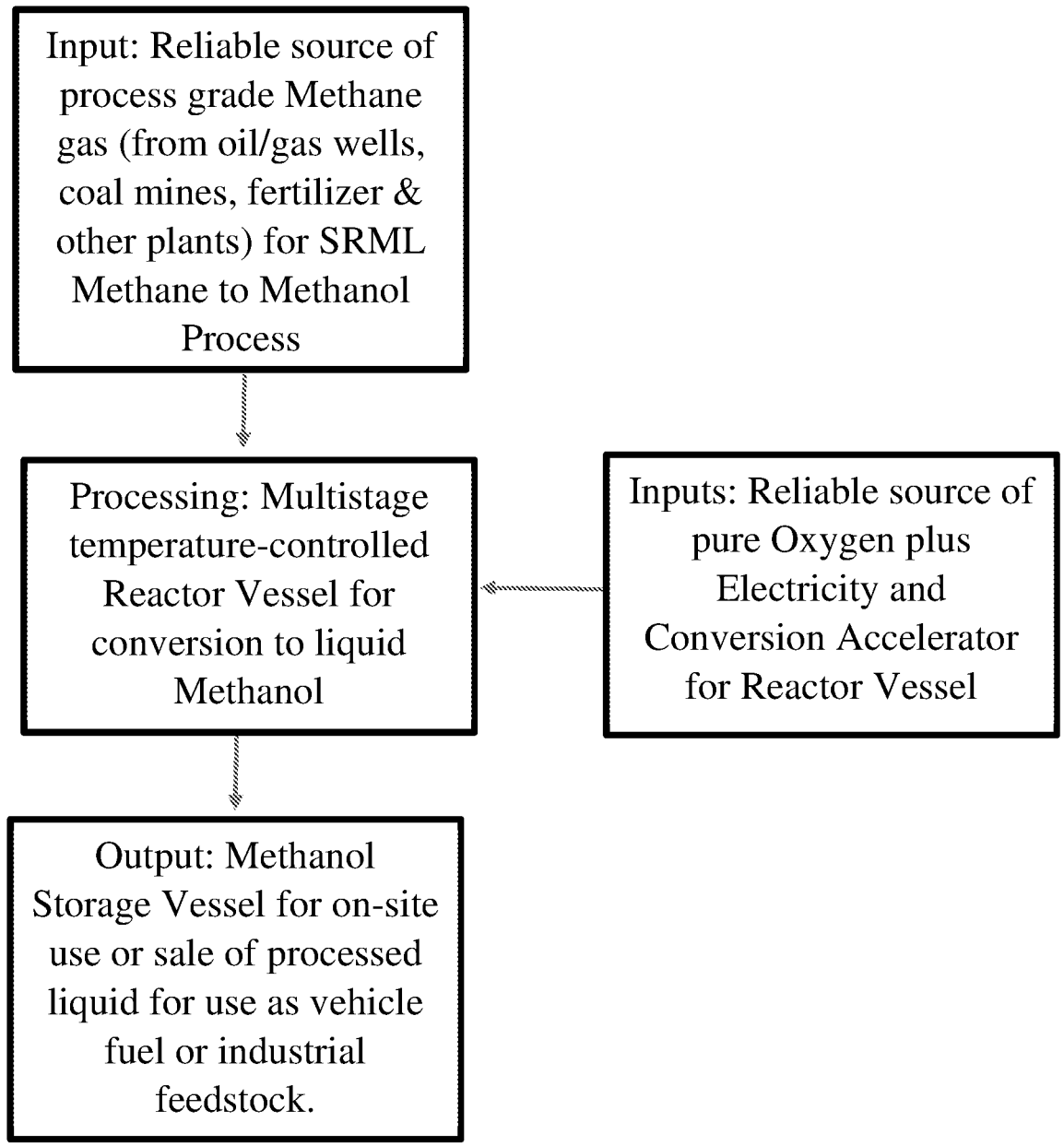

METHANE TO METHANOL CONVERSION

This application claims the benefit under 35 USC 119 (e) of Provisional application 63/167,168 filed Mar. 29th 2021.

This invention relates to a method for conversion of methane to methanol.

BACKGROUND OF THE INVENTION

There is an abundance of methane in natural gas reserves and shale gas, which is flared presently in many locations as there is no close market or gathering systems available to use the gas for heating. The gathering system has to be constructed in any case, and under normal conditions a scrubbing plant has to be built to amine scrub the acid gases out of the gas at the well head. This has to be done to get pipeline quality in the methane and the sulphur compounds and carbon dioxide have to be removed. However, methane has so much more potential.

Presently the processes available have proven difficult and costly due to the relative inertness of methane with its strong C—H bonds. CH4 presently requires that oxidative coupling and direct dehydrogenation processes have to be carried out at temperatures between 600 and 1100 degrees C. in order to break them apart.

Other processes have been investigated to convert methane to methanol, allowing liquid methanol to be gathered and shipped by transport to the chemical industry affording a higher price to the producer.

It is known that molecular oxygen and carbon monoxide can be used for the direct conversion of methane to methanol in a process which is catalyzed by supported mononuclear rhodium dicarbonyl species, anchored on the internal pore walls of zeolites supports that were suspended in water under mild pressure (20 to bar) and temperature (110 to 150 degrees C.).

The same catalyst also produces acetic acid through a different reaction scheme that does not involve methanol as an intermediate. Carbon monoxide is essential to the catalytic reaction, which is heterogeneous. Tuning the reaction to either methanol or acetic acid is possible by properly controlling the operating conditions, especially the acidity of the support. Even after many hours of reaction, there is no leaching of the catalyst in the water.

SUMMARY OF THE INVENTION it is an object of the present invention to provide a method to convert methane to methanol that does not involve high temperature conversion with expensive noble metal catalysts.

According to the invention there is provided a method for converting methane into methanol using an oxidizing agent and a catalyst of single iron atoms embedded in graphene.

Preferably the method is carried out at room temperature in the range 21 to 30 degrees C.

Preferably the method is carried out at a pressure less than three bars.

Preferably the oxidizing agent is pure oxygen.

Preferably the oxygen expands as it vaporizes from storage to provide sufficient line pressure to blend the oxygen required.

Preferably the oxygen is fed to the fixed bed reactors from cryogenic storage, vaporized, and heated with an electric line heater.

Preferably the supply gas of methane is separated using molecular sieve separations.

Preferably the catalyst is carried on a bed of zeolite which removes nitrogen and nitrogen compounds in adsorption process, as well as some sulphur and a good percentage of carbon dioxide.

Preferably the catalyst is Fe—N—C and a further improvement of pristine Fe—N—C is obtained through using $Ti_3C_2T_x$ MXene as a support.

Preferably the catalyst comprises a highly dispersed single $FeN_4$ center anchored on graphene.

Preferably the catalyst is synthesized by high-energy ball milling of iron phthalocyanine (FePc) and GNs.

Preferably the yield of C1 oxygenated products increases as the Fe amount increases from 1.5 to 4.0 wt %.

Preferably the Fe amount is of the order of 2.7 wt % Fe in $FeN_4$/GN.

Preferably the yield of C1 oxygenated products increases with the reaction time, reaching the highest at 10 hr.

Preferably the reaction is carried out in a vessel which is double walled and contains an insulating material between the walls.

Preferably hot water/steam lines are provided to maintain operating temperature at a required value in adverse conditions.

Preferably the hot water/steam lines are wrapped around the inner wall of the vessel which contains the catalyst in a bed and distillation like trays.

Preferably a gap between the walls is filled with perlite insulation

Preferably the reaction is operated in a stainless-steel autoclave containing a Teflon liner vessel.

Preferably a support for the catalyst comprises a wire mesh support system to allow flow of converted methanol liquid into distillation trays installed in the vessel and butted to a wall of the vessel for collection at a bottom of the vessel and pumping into final storage.

Preferably a methane line entering the reactor is fitted with spray heads to give even distribution of the gases over a bed of the catalyst.

BRIEF DESCRIPTION OF THE DRAWINGS

FIG. 1 is a process schematic showing the steps of the method.

DETAILED DESCRIPTION

Methane is gathered at the well-head, transported to the process site, and cleaned up to pipeline quality. As most contaminants will be as acid gases; carbon dioxide and sulphur compounds such as $SO_2$. Arrangements are provided to clean up the gases to achieve beyond pipeline purity by utilizing molecular sieve separations rather than trying to add facilities such as amine scrubbing. This is done to achieve purity, and reduce costs using new molecular sieves. As natural gas is primarily methane, it compresses for storage at a ratio of 10 to 1 thus allowing storage presently available for commercial users, of standard tankage being 30,000 gals. each. The number of these storage tanks for methane is determined by the well pressures and off gassing, providing a pre-determined calculation of gas in the well.

Standard 2 inch round mechanical 16 gauge 0.065 wall thickness I.D.1.870 seamless piping is used to handle flow rates of gases up to 14,870 s.cf. per hour. The pipe is cleaned and free of any hydrocarbon and butt welded, using shielding gas of argon and 2% oxygen, with wire providing for 87,000 lbs tensile strength, CVN. 40 lbs. at −40 degrees C. as welded, with joint preparation at each seam. The clean methane flows into a gas compressor (explosion-proof for methane natural gas), sized to provide a line pressure and flow rate of 30 lbs. per sq. in. and a flow of 12,500 scf. per hr.

The oxidizing agent is pure oxygen where the supply is preferably of copper tubing schedule 40, cleaned and prepared with silver brazed joints. Oxygen is fed to the fixed bed reactors from cryogenic storage, vaporized, and heated with an electric line heater. The expansion of the oxygen as it vaporizes provides sufficient line pressure to blend the oxygen required for at least two fixed-bed reactors. The oxygen supply, and cryogenic storage tank can be obtained from a commercial industrial gas company.

As the methane flows are determined, the molecular count of the $CH_4$ is calculated, and the flows set for the oxygen is calculated based upon the hydrogen molecule becoming free over the catalyst and bonding to the free oxygen molecule, forming the $CH_3OH$.

The reaction occurs on fixed-bed reactors which can receive the methane and oxygen through controlled Fischer pressure flow rate regulators. The molecular flow of each is set and controlled by the Fischer controller/flow meters. As a part of the fixed-bed reactor, the internal tubing taking in the oxygen and distributing it at each level where the three catalyst beds are located, along with the liquid receiver trays, and are a part of the assembly of the Fixed-Bed reactors/stripper. The oxygen flows to each of the three catalyst beds is calculated and timed to meet the flow of methane on the bed above and is dispersed evenly over each respective bed, by a spray head of 304 SS with 0.7938 mm holes (1/32") across each catalyst bed. The trays below each bed will take and drain off the methanol as it leaves the catalyst bed and the reaction is complete. The reactor does not operate above three bars, so no additional items are required when also considering the reactor/stripper functions at 21 to 30 degrees C., or from 294.15 to 303.15 degrees Kelvin. This is the tremendous advantage of this catalyst and chemical shift, the low temperatures and pressure required to achieve the shift, and the low cost of the catalyst.

The catalyst itself is the critical factor and is developed and put together as follows:

The $FeN_4$ ground apart particles embedded in the lattice structure of graphene (GNs) is prepared by a well-tested procedure.

The highly dispersed single $FeN_4$ center anchored on graphene is synthesized by high-energy ball milling of iron phthalocyanine (FePc) and GNs. The atomic force microscopy (AFM) image of $FeN_4$/GN shows the typical structure of GNs, and a sub-angstrom resolution high-angle annular dark-field scanning transmission electron microscopy (HAADF-STEM) image displays single-atom iron sites distributed homogeneously in GNs.

Iron—nitrogen—carbon (Fe—N—C) is hitherto considered as one of the most satisfactory alternatives to platinum for the oxygen reduction reaction (ORR). Major efforts currently are devoted to the identification and maximization of carbon-enclosed $FeN_4$ moieties, which act as catalytically active centers. However, fine-tuning of their intrinsic ORR activity is required.

Herein, a twofold activity improvement of pristine Fe—N—C through introducing Ti3C2Tx MXene as a support is realized. A series of spectroscopy and magnetic measurements have shown that the marriage of $FeN_4$ moiety and MXene can induce remarkable Fe 3d electron delocalization and spin-state transition of Fe (II) ions. The lower local electron density and higher spin state of the Fe (II) centers greatly favor the Fe dz2 electron transfer, and lead to an easier oxygen adsorption and reduction on active $FeN_4$ sites, and thus an enhanced ORR activity. The optimized catalyst shows a twofold and fivefold higher specific ORR activity than those of pristine catalyst and Pt/C, respectively, even exceeding most Fe—N—C catalysts ever reported. This work opens up a new pathway in the rational design of Fe—N—C catalysts, and reflects the critical influence of Fe 3d electron states in $FeN_4$ moiety supported on MXene in ORR catalysis.

Firstly, graphene sheets are purchased and the microscopic particles of iron phthalocyanine are imbedded in the graphene sheets by the supplier of the graphene. In brief, the highly dispersed single $FeN_4$ center anchored on graphene is synthesized by high-energy ball milling of iron phthalocyanine (Fe Pc) and GNs. The atomic force microscopy (AFM) image of $FeN_4$/GN show the typical structure of GNs, and a sub-angstrom resolution high-angle annular dark-field scanning transmission electron microscopy (HAADF-STEM) image displays single-atom iron sites distributed homogeneously in GN.

The catalytic oxidation of methane is carried out in a fixed bed reactor. Thus the reactor provides a separation column designed with temperature and pressure variability to be built in with cryogenic oxygen supply as the oxidant. Each reactor of two such reactors with three levels of catalyst beds on retaining trays, and distillation trays installed below.

Each fixed bed reactor has a separate line electric heater of a boiler with the steam lines encasing the fixed-bed reactor to maintain temperatures. The liquid and gas products are measured at the start-up by Hand $^{13}C$ NMR, time-of-flight mass spectrometry (TOF-MS), and gas chromatography, respectively. Combining $^{13}C$ NMR, $^{13}C$ DEPT-135 (distortion less enhancement by polarization transfer), 1HNMR, and 2D1 H-$^{13}C$ hetero nuclear multiple-quantum correlation experiments, methane can be efficiently oxidized to C1 oxygenated products over a $FeN_4$/GN catalyst with a turnover frequency (TOF) of 0.47 hr1where TOF=mol of product (mol of Fe)1hr1; CH3OH, $CH_3OOH$, $HOCH_2OOH$, and HCOOH is the major products in the liquid phase. TOF-MS with a vacuum ultraviolet lamp as the ionization source is used to further confirm the structures of C1 oxygenated products. The featured peaks match well with $CH_3OH$, $CH_3OOH$, $HOCH_2OOH$, and HCOOH from the NMR data.

Considering the catalyst itself contains carbon sources, control experiments by using $N_2$, $CH_4$, and $^{13}CH_4$ as the reactant gas, where only $^{13}CH_4$ can produce 13C oxygenated products provides results which indicate that C1 oxygenated products come from the oxidation of $^{13}CH4$ rather than from the catalyst itself. In addition, a reusability test reveals that the $FeN_4$/GN catalyst almost preserves its initial catalytic activity after six cycles, and the X-ray adsorption fine-structure spectra indicates that, after the reusability test, the catalyst almost retains the same chemical state and coordination information as the original catalyst, demonstrating its good structural stability and reusability.

Besides the $FeN_4$/GN catalyst, the catalytic performance of other control catalysts has been reviewed, i.e., graphite, graphene, and different 3d metal-N4 confined in graphene ($MnN_4$/GN, $CoN_4$/GN, $NiN_4$/GN, and $CuN_4$/GN); where their structures are almost the same as the $FeN_4$/GN with metal-$N_4$ centers embedded in the graphene nano sheets. Results shows that none could catalyze methane conversion except the $FeN_4$/GN catalyst. The yield of C1 oxygenated products increase as the Fe amount increases from 1.5 to 4.0 wt %, where 2.7 wt % Fe in $FeN_4$/GN the optimum according to the calculated turnover number (TON) data. That is because the increase in Fe content results in more active sites at low Fe content, whereas the dispersion of active sites decreases at high Fe content as a result of agglomeration. In addition, the activity of Fe Pc on methane oxidation from modelling was evaluated, which showed that the TON for Fe Pc was far less than that for $FeN_4$/GN catalysts. That is because Fe Pc had poor ability to activate methane. The initial yield of C1 oxygenated products increases with the reaction time, reaching the highest at 10 hr, and then decays with the reaction time. Meanwhile, $CO_2$ in gas phase increases with the reaction time, indicating that the liquid C1 oxygenated products can be further oxidized to $CO_2$ with longer reaction time, and the reaction time can be controlled to get maximum C1 oxygenated products.

The selectivity of C1 oxygenated products is around 94%, and the $CO_2$ selectivity is only 6% for reaction for 10 hr. Compared with the $FeN_4$/GN catalyst promotes methane conversion under milder conditions with lower $CO_2$ selectivity. Structural features and catalytic performance of $FeN_4$/GN-2.7(A) An HAADF-STEM image of $FeN_4$/GN-2.7. The results show some single iron atoms in the matrix of graphene nanosheets. The model of $FeN_4$/GN. $^{13}C$ NMR and $^{13}C$ DEPT-135 spectra, and TOF-MS data, obtained from typical reaction products of methane oxidation. The process development shows a symbol which represents one water molecule. (D) $^{13}C$ NMR spectra obtained from $N_2$, $CH_4$, and $13CH_4$ as reaction gas.

Catalytic performance of graphite, graphene, $FeN_4$/GN, and other metal-$N_4$/GN for $CH_4$ oxidation. Reaction conditions in: 50 mg catalyst, 5 mL $H_2O$, 5 mL $H_2O_2$ (30%), and 2 MPa reaction gas in a fixed-bed reactor.

Catalyst trays are fabricated from 304 stainless steel of 22-gauge material and will slide on to the retaining brackets specified and fabricated for the interior of the vessel itself; tight to all walls and sealed, with drainage only through the three layers of catalyst beds of 44.45 mm depth (1.75 inches). At the pressures and temperature the three beds at this depth and the two reactors in use, provide for adequate throughput overcoming the lengthy residence time encountered in development. The drainage of methanol is into standard 304 S.S., 20-gauge, distillation trays, draining through channels and tubing, to the bottom of the reactor. Pumps are installed to move the methanol; firstly, from the first catalytic reactor to the second, and secondly from the catalytic reactors into the storage vessel. The storage vessel is located over one hundred feet from the actual processing in order to comply with safety.

In order to study the reaction mechanism, the evolution of liquid products in a high-pressure reaction can be tracked. In brief, the products can be efficiently extracted by a capillary and analyzed in real time throughout the reaction. During the reaction, $CH_3OH$ and $CH_3OOH$ increased gradually over time. $HOCH_2OOH$ and $HCOOH$ almost did not change in the first 10 min, which suggests that $CH_4$ is first oxidized to $CH_3OH$ and $CH_3OOH$. In addition, the increasing rate of $CH_3OH$ in the first 300 min was greater than in the last 300 min. In the last 300 min, $HOCH_2OOH$ and $HCOOH$ increased significantly, which shows that $CH_3OH$ from $CH_4$ oxidation is further oxidized to $HOCH_2OOH$ and $HCOOH$. In order to confirm the hypothesis, we used $CH_3OH$ directly as the reactant instead of $CH_4$. Accordingly, $^{13}C$ NMR and $^{13}C$ DEPT-135 present three peaks corresponding to $CH_3OH$, $HOCH_2OOH$, and $HCOOH$, indicating that $CH_3OH$ can be converted into $HOCH_2OOH$ and $HCOOH$ over the catalyst, which agrees well with the results of in operando TOF-MS. Therefore, it can be deduced that $CH_4$ was first oxidized to $CH_3OH$ and $CH_3OOH$, and then the $CH_3OH$ generated was further oxidized to $HOCH_2OOH$ and $HCOOH$.

To understand the mechanism for the selective oxidation of methane on the $FeN_4$/GN structure, density functional theory (DFT) calculations were used to build a $FeN_4$ structure embedded in the matrix of graphene. Under the reaction conditions, $O_2$ molecules can be easily absorbed on the active Fe sites and decompose into $H_2O$ and an adsorbed O atom. Each active Fe site can absorb two O atoms at each side with a total energy decrease of 2.63 eV shows that the electronic states of O—$FeN_4$—O around the Fermi level increase significantly in comparison with those of $FeN_4$ and $FeN_4$—O, suggesting that the O—$FeN_4$—O structure is more active than others.

The reaction pathway of methane conversion was then calculated on the O—FeN structure. Previous work reported that there were two possible pathways in the hydroxylation reactions catalyzed by the O—$FeN_4$—SH site of P450, i.e., a concerted mechanism and a radical pathway. For the O—$FeN_4$—O structure, the energy barrier of the concerted mechanism is as high as 1.91 ev, more than twice higher than the formation of a methyl radical, which is only 0.79 ev. Therefore, methane activation over the O—$FeN_4$—O structure should proceed along the radical mechanism, and the rate-determining step is C—H bond cleavage (0.79 eV). After the first C—H bond of methane is activated, the O—$FeN_4$—O active site can continue to activate other C—H bonds, generating a series of oxidation products show that the methyl radical generated can combine with hydroxyl and hydroperoxide groups easily to form $CH_3OH$ and $CH_3OOH$, and the CH3OH can be further converted to $HOCH_2OOH$ and $HCOOH$ via the hydroxymethyl radical, which was confirmed by the analysis in electron paramagnetic resonance experiments The energy required for each step is very low, no more than 0.2 eV, thus enabling the selective oxidation of methane at temperatures of 21 to 25 degrees C.

In addition, we also employed DFT calculations to study the process of methane activation on the FePc molecule and other $MN_4$/GN (M=Cr, Mn, Co, Ni, Cu) catalysts. It was found that methane oxidation on O—$FeN_4$—O was easier than that on the O—FePc-O structure, suggesting that the graphene network can improve the catalytic activity of the $FeN_4$ center for methane activation. For other $MN_4$/GN structures, the formation energies of O—$MN_4$-O structures indicated that only Cr. Mn, Fe, and Co can form their corresponding O—$MN_4$-O O—$MN_4$-O structures. Furthermore, according to the kinetic equation of methane activation (see Supplemental Information for details), the formation energy of the O—$MN_4$-O active site (Gf) can be used as a descriptor for methane oxidation for a broad range of catalytic materials. A good catalyst should have a moderate Gf, resulting in a volcano curve between the methane activation rate The relationship between the methane activation rate (log[rate]) and the formation energy of the active site GO presents a volcano curve. The Gf and activation rate of the calculated and structures are shown on the volcano. (log [rate]) and Gf. As the corresponding activity of different O—$MN_4$—O structures are plotted on the volcano curve. Among all $MN_4$—O structures (Cr, Mn, Fe, and Co), O—$FeN_4$—O has the best ability to compromise all barriers in the reaction pathways. Therefore, the $FeN_4$/GN catalyst possesses the best activity for $CH_4$ conversion, confirming the experimental results.

In summary, it is demonstrated that methane can be directly converted to C1 oxygenated products at room temperature over graphene-confined single iron atoms. The unique O—FeN$_4$—O structure formed is able to active the C—H bond of methane to form the methyl radical with a low reaction energy barrier (0.79 eV). The methyl radical is first converted into CH$_3$OH and CH$_3$OOH, and CH$_3$OH can be further converted to HOCH$_2$OOH and HCOOH on the O—FeN$_4$—O structure, as illustrated by TOF-MS, $^{13}$C NMR, and DFT calculations. The moderate formation energy of O—FeN$_4$—O results in its unique activity for methane conversion at room temperature in comparison with that of other graphene-confined first transition metals. These findings provide a new route to understanding and designing highly efficient non-precious catalysts for methane conversion in mild conditions.

EXPERIMENTAL PROCEDURES

Raw Materials

Graphite flake (99.8%, metal basis) was purchased Iron (II) phthalocyanine (FePc), copper(II) phthalocyanine (CuPc), cobalt(II) phthalocyanine (CoPc), manganese(II) phthalocyanine (MnPc), and nickel(II) phthalocyanine (NiPc) were purchased. They were commercial materials of analytical grade and were used as received without further purification.

Synthesis of Catalysts

FeN$_4$/GN samples with different Fe content were prepared by a well-tested procedure. In a typical experiment, first, 2.0 g graphite flake and 60 g steel balls (1-1.3 cm in diameter) were put into hardened steel under Ar (99.999%). The ball milling process was carried out at 450 rpm for 20 hr to obtain GNs. Then 0.6 g FePc, 1.4 g GN, and 60 g steel balls (1-1.3 cm in diameter) were further ball milled at 450 rpm for 20 hr to obtain FeN$_4$/GN-2.7. MN$_4$/GN, CoN$_4$/GN, NiN$_4$/GN, and CuN$_4$/GN were synthesized in the same way as the preparation of FeN$_4$/GN-2.7 with MnPc, COPc, NiPc, and CuPc in place of FePc, respectively Characterization STEM was performed on a JEOLARM200F equipped with double aberration correctors and a cold field emission gun operated at 80 kV. STEM images were recorded with an HAADF detector with a convergence angle of 30 mrad and a collection angle between 90 and 370 mrad. Tapping-mode AFM measurements were conducted with a Bruker Metrology Nanoscope III-D atomic force microscope operated under ambient conditions. Commercial tapping-mode tips made of phosphorus (n)-doped Si were supplied from Veeco with 115-135-gm-long cantilevers with resonance frequencies of 293-387 kHz and spring constants of 20-80 N/m.

Catalytic Methane Oxidation Evaluation

The methane oxidation reaction is carried out in a stainless-steel autoclave containing a Teflon liner vessel (working volume, 50 mL). First, the vessel is charged with 50 mg catalyst, 5 mL deionized water, and 5 Ml H$_2$O$_2$ (30%); then the autoclave is flushed with methane three times and pressurized to 2 MPa CH$_4$ (89.9%, N$_2$ as balance gas). The reaction mixture is heated to the desired temperature (typically 250 C). The products will be cooled down in ice-water for 30 min before analysis before being filtered and analyzed.

DFT Calculations

DFT calculations are performed with the Vienna ab initio simulation package (VASP)32 according to the projector-augmented wave method. All calculations are based on the same generalized gradient approximation method with the Perdew-Burke-Ernzerhof34 functional for the exchange-correlation term. The plane-wave cut-off was set to 400 eV. The Brillouin zone was sampled by a 6×6×1 k-point grid for the calculations of charge density and a 2×2×1 Monkhorst-Pack3S k-point grid for structure optimizations. During geometry optimization, the convergence of energy and forces were set to 1×10$^{-4}$ ev and 0.05 eV/A, respectively. The transition states of chemical reactions were located through the climbing image nudged elastic band method, in which the convergence forces were set to 0.1 eV/Å. A periodically repeated single-layer graphene model was built with a unit cell size of 5×5 and a vacuum slab height of 17 Å.

Kinetic analysis details for the volcano curve in are as follows:

$$\text{rate} = v k_B T / h e^{-\Delta G_a / k_B T}$$

where $$v = \frac{c((H_2O_2)/c((H_2O_2)e^{-G_f/k_B T}}{1 + c(H_2O_2)/c(H_2O_2)e^{-G_f/k_B T}}$$

The scaling relationship between the activation free energy difference (AGa) and the formation energies of the active sites (Gf) was cited from Nørskov et al. According to the reaction conditions, c(H$_2$O$_2$)/c(H$_2$O)=1, T=298

The catalytic reformer/strippers are double jacketed to allow the hot water/steam lines to maintain operating temperatures especially in winters and adverse conditions. The hot water lines are wrapped around the inner vessel containing the catalyst bed and distillation like trays. The second vessel will allow for a 63.5-millimeter (2.5 in) gap between the walls which is filled with perlite insulation.

The inner vessel is constructed with FM 45 steel plate, 5/16 in. (7.9375 mm) thick, roll formed to be 1.8288 meter in diameter (6') the joints are plate edge prepared providing a flat strong weld. The vessel is constructed with support for the installation of the mesh supporting the graphene and iron sheet catalyst to the depth specified herein above. It is butted to all the walls, and sealed to ensure the methane is forced to flow over and through the catalytic bed. The support and wire mesh support system allow flow of converted methanol liquid into the distillation trays installed butted to the walls also and draining to the bottom of the column for pumping into final storage.

The exterior vessel covering the main catalytic convertor is of 4.7625 millimeters thick, (3/16), steel formed and welded to provide the protective jacket. Both the inner and outer vessels have access provided through the top to change or service catalysts or repair.

The top is dished to provide additional support and strength to the reactor vessel.

The capital equipment is as shown herein is as follows:

Storage vessel for compressed natural gas/methane as CNG is stored at the ratio of 10-1 reducing need for huge tankage. A tank of 40,000 gals is adequate on site.

From storage, methane flows through a pump/stabilizer to control line pressures and flows to each of the heaters and reactors.

Electric heaters and boilers are installed on each line just immediately as the gas is entering the reactor/convertor. There are pumps installed to circulate the hot water/steam at low pressure through a flexible copper line 12.7 mm in diameter, (½"), which are wrapped around, (but not touching) the inner vessel. The flows have regulation on them, controlling temperature in the reactor during winter, or adverse weather conditions. Temperatures can run from 21 to 25 degrees C. The water returns to the reservoir on the boiler as a part of the electric heater-boiler system The outer shell, or tank, is of a diameter of 50.8 mm (2 inch) larger than the inner, to provide for the perlite insulation barrier to be put in place.

Both the methane and oxygen lines have emergency shut-off valves as the lines enter the top of each catalytic reactor. These automatically shut when temperature rise above 35 degrees C.

Both the methane and oxygen flows are controlled by Fischer flowmeter (molecular) control, and pressure regulators. Four of these are required and set tying into the to-be-designed computer-controlled system.

The oxygen line is preferably steel, but must be cleaned and free of any hydrocarbon or flammable particles.

The oxygen, as well as the methane line entering the inner reactor vessel, is fitted with spray heads comprised of 304 SS tubes with holes drilled to give even distribution of the gases over the catalyst bed.

The catalytic reactor/convertors each have valving at the bottom to allow the methanol to be taken off and controlled.

The methanol leaving the tank goes through the line pump which is specifically built for LPG thus increasing line pressure to take the methanol to storage.

The invention claimed is:

1. A method for converting methane into methanol using an oxidizing agent and a catalyst of single iron atoms embedded in graphene;
    wherein the method is carried out at room temperature;
    wherein the method is carried out at a pressure less than three bars;
    and wherein the catalyst is Fe—N—C using $Ti_3C_2T_x$ MXene as a support.

2. A method for converting methane into methanol using an oxidizing agent and a catalyst of single iron atoms embedded in graphene;
    wherein the method is carried out at room temperature;
    wherein the method is carried out at a pressure less than three bars;
    and wherein the catalyst is Fe—N—C using $Ti_3C_2T_x$ MXene as a support;
    and wherein the oxidizing agent is pure oxygen.

3. The method according to claim 2 wherein the oxygen expands as it vaporizes from storage to provide sufficient line pressure to blend the oxygen required.

4. The method according to claim 3 wherein the oxygen is fed to the fixed bed reactors from cryogenic storage, vaporized, and heated with an electric line heater.

5. The method according to claim 1 wherein the supply gas is separated using molecular sieve separations.

6. The method according to claim 1 wherein the catalyst is carried on a bed of zeolite which removes nitrogen and nitrogen compounds in adsorption process, as well as some sulphur and carbon dioxide.

7. The method according to claim 1 wherein the catalyst is synthesized by ball milling of iron phthalocyanine (FePc) and GNs.

8. The method according to claim 1 wherein the Fe content is in the range from 1.5 to 4.0 wt %.

9. The method according to claim 1 wherein the Fe content is of the order of 2.7 wt %.

10. The method according to claim 1 wherein the reaction time is of the order of 10 hr.

11. The method according to claim 1 wherein the reaction is carried out in a vessel containing the catalyst in a bed where the vessel is double walled and contains an insulating material between the walls and wherein hot water/steam lines are provided to maintain operating temperature at a required value in adverse conditions where the hot water/steam lines are wrapped around the inner wall of the vessel.

12. The method according to claim 11 wherein the vessel comprises a stainless-steel autoclave containing a Teflon liner.

13. The method according to claim 1 wherein a support for the catalyst comprises a wire mesh support system to allow flow of converted methanol liquid into distillation trays installed in the vessel and butted to a wall of the vessel for collection at a bottom of the vessel and pumping into final storage.

14. The method according to claim 1 wherein a methane line entering the reactor is fitted with spray heads to give even distribution of the gases over a bed of the catalyst.

15. A method for converting methane into methanol using an oxidizing agent and a catalyst of single iron atoms embedded in graphene;
    wherein the method is carried out at room temperature;
    wherein the method is carried out at a pressure less than three bars;
    and wherein the catalyst is carried on a bed of zeolite which removes nitrogen and nitrogen compounds in adsorption process, as well as some sulphur and carbon dioxide.

16. The method according to claim 15 wherein the catalyst is carried on a bed of zeolite which removes nitrogen and nitrogen compounds in adsorption process, as well as some sulphur and carbon dioxide and wherein a methane line entering the reactor is fitted with spray heads to give even distribution of the gases over the bed of the catalyst.

17. A method for converting methane into methanol using an oxidizing agent and a catalyst of single iron atoms embedded in graphene;
    wherein the method is carried out at room temperature;
    wherein the method is carried out at a pressure less than three bars;
    and wherein the reaction is carried out in a vessel containing the catalyst in a bed where the vessel is double walled and contains an insulating material between the walls;
    and wherein hot water/steam lines are provided to maintain operating temperature at a required value in adverse conditions where the hot water/steam lines are wrapped around the inner wall of the vessel.

18. The method according to claim 17 wherein the catalyst is carried on a bed of zeolite which removes nitrogen and nitrogen compounds in adsorption process, as well as some sulphur and carbon dioxide and wherein a methane line entering the reactor is fitted with spray heads to give even distribution of the gases over the bed of the catalyst.

19. A method for converting methane into methanol using an oxidizing agent and a catalyst of single iron atoms embedded in graphene;

wherein the method is carried out at room temperature;
wherein the method is carried out at a pressure less than three bars;
and wherein a support for the catalyst comprises a wire mesh support system to allow flow of converted methanol liquid into distillation trays installed in the vessel and butted to a wall of the vessel for collection at a bottom of the vessel and pumping into final storage.

20. The method according to claim 19 wherein the catalyst is carried on a bed of zeolite which removes nitrogen and nitrogen compounds in adsorption process, as well as some sulphur and carbon dioxide and wherein a methane line entering the reactor is fitted with spray heads to give even distribution of the gases over the bed of the catalyst.

* * * * *